US009726595B2

(12) United States Patent
Kazumura et al.

(10) Patent No.: US 9,726,595 B2
(45) Date of Patent: Aug. 8, 2017

(54) MEASUREMENT APPARATUS

(71) Applicant: HAMAMATSU PHOTONICS K.K., Hamamatsu-shi, Shizuoka (JP)

(72) Inventors: Kimiko Kazumura, Hamamatsu (JP); Hiroshi Tsuchiya, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/234,339

(22) Filed: Aug. 11, 2016

(65) Prior Publication Data

US 2017/0052109 A1 Feb. 23, 2017

(30) Foreign Application Priority Data

Aug. 17, 2015 (JP) .................. 2015-160319

(51) Int. Cl.
*G01N 21/64* (2006.01)
*G01N 21/01* (2006.01)
*G01N 21/76* (2006.01)
*G01N 33/49* (2006.01)

(52) U.S. Cl.
CPC ............. *G01N 21/01* (2013.01); *G01N 21/64* (2013.01); *G01N 21/76* (2013.01); *G01N 33/49* (2013.01)

(58) Field of Classification Search
CPC ............................... G01N 21/64; G01N 21/76
See application file for complete search history.

(56) References Cited

U.S. PATENT DOCUMENTS

2010/0260422 A1* 10/2010 Ito .................... C12M 41/14
382/190

FOREIGN PATENT DOCUMENTS

| JP | S58-137758 A | 8/1983 |
|---|---|---|
| JP | 4255121 B2 | 4/2009 |
| JP | 5237809 B2 | 7/2013 |
| WO | WO-2008/016096 A1 | 2/2008 |

* cited by examiner

*Primary Examiner* — Kiho Kim
(74) *Attorney, Agent, or Firm* — Drinker Biddle & Reath LLP (57) ABSTRACT

A measurement apparatus includes a sample stage, an excitation unit, a light receiving unit, a stimulant applying nozzle, and a spray nozzle in a measurement space inside a body case, and also includes a heating unit and a gas supplying unit. The body case includes an inner case surrounding the measurement space, and an outer case surrounding the inner case to shield the measurement space from light from the outside and seal the measurement space. The heating unit is disposed between the inner case and the outer case and adjusts temperature in the measurement space through the inner case. The gas supplying unit supplies gas having controlled temperature and humidity into the measurement space and adjusts temperature and humidity in the measurement space.

11 Claims, 4 Drawing Sheets

MEASUREMENT APPARATUS

BACKGROUND OF THE INVENTION

Field of the Invention

The present invention relates to an apparatus that measures light generated in a sample.

Related Background Art

An invention of an apparatus that measures light (e.g. fluorescence or chemiluminescence) generated in a sample to analyze the sample is disclosed in Patent Documents 1 and 2. The apparatus of the inventions disclosed in Patent Documents 1, 2 measures light generated in a specific component in blood as a sample to measure concentration of the specific component based on a measurement value of the light. In these inventions, in order to perform measurement with higher accuracy, a measurement space for disposing the sample and the like is covered with a case for light-shielding to prevent stray light from coming into the measurement space from the outside, as well as for controlling temperature of the sample.

Patent Document 1: Japanese Patent Publication No. 4255121

Patent Document 2: Japanese Patent Publication No. 5237809

Patent Document 3: Japanese Patent Application Laid-Open Publication No. S58-137758

SUMMARY OF THE INVENTION

The present inventors have found a problem to be described below in an apparatus that measures light generated in a sample (e.g. blood) placed in a measurement space covered with a case to analyze the sample such as the apparatuses described in Patent Documents 1, 2.

For example, a sample as a measurement object including liquid (blood plasma) and solid (blood cell) such as blood causes the liquid to evaporate and varies concentration of the sample during a measurement period if measurement takes a long time, resulting in an inaccurate measurement result. In addition, the solid may sometimes aggregate in a certain region in the sample during the measurement period to also cause an inaccurate measurement result. To solve this problem of the aggregation, gas may be sprayed on a sample to agitate the sample for uniformity as the invention disclosed in Patent Document 3. However, spraying the gas may cause liquid to evaporate, and thus concentration of the sample varies to cause an inaccurate measurement result.

The present invention has been made in order to solve the above problem, and an object thereof is to provide a measurement apparatus capable of accurate measurement.

A measurement apparatus according to the present invention includes (1) a sample stage on which a sample is placed, (2) a light receiving unit receiving light generated in the sample, (3) a spray nozzle spraying gas on the sample to agitate the sample, (4) a body case including an inner case that surrounds a measurement space in which the sample stage, the light receiving unit, and the spray nozzle are disposed, and an outer case that surrounds the inner case, the body case shielding the measurement space from light from the outside, (5) a heating unit being disposed between the inner case and the outer case and adjusting temperature in the measurement space through the inner case, and (6) a gas supplying unit supplying gas having controlled temperature and humidity into the measurement space and adjusting temperature and humidity in the measurement space.

The present invention enables the measurement space, in which the sample is placed, to be maintained to have a constant temperature and a constant humidity to prevent evaporation of the sample to enable accurate measurement.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE EMBODIMENTS

Hereinafter, embodiments of the present invention will be described in detail with reference to the accompanying drawings. In description of the drawings, the same elements will be denoted by the same reference signs, without redundant description.

First Embodiment

Figure 1:
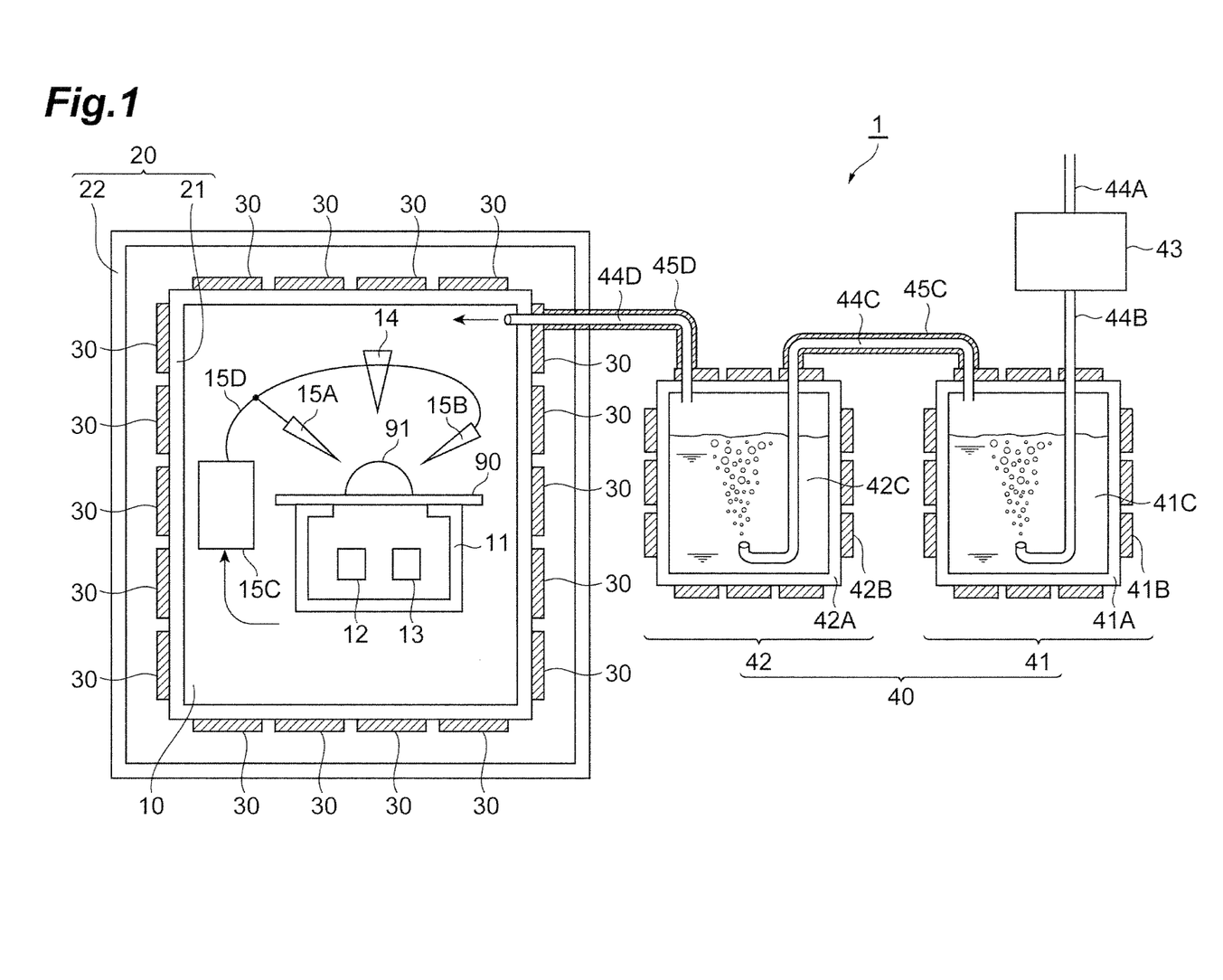
FIG. 1 illustrates a configuration of a measurement apparatus 1 of a first embodiment.

FIG. 1 illustrates a configuration of a measurement apparatus 1 according to a first embodiment. The measurement apparatus 1 includes a sample stage 11, an excitation unit 12, a light receiving unit 13, a stimulant applying nozzle 14, spray nozzles 15A and 15B, and the like in a measurement space 10 inside a body case 20. The measurement apparatus 1 further includes a heating unit 30 and a gas supplying unit 40.

The sample stage 11 allows a sample 91 as a measurement object to be mounted thereon. The sample 91 is preferably placed on the sample stage 11 while placed in a container or on the container. As the container, a plate-type container (e.g. a preparation 90) may be preferably employed to improve measurement efficiency.

The excitation unit 12 irradiates the sample 91 with excitation light to excite a fluorescent indicator contained in the sample 91, for example, to generate fluorescence from the fluorescent indicator. The light receiving unit 13 receives and detects light generated in the sample 91. The light received by the light receiving unit 13 may be, for example, fluorescence generated from the fluorescent indicator contained in the sample 91, or chemiluminescence generated from a chemiluminescent indicator contained in the sample 91.

The excitation unit 12 preferably irradiates the sample 91 with the excitation light from below, and the light receiving unit 13 receives the light below the sample 91. While the stimulant applying nozzle 14 and the spray nozzles 15A and 15B are provided above the sample 91, the excitation unit 12 and the light receiving unit 13 are provided below the sample 91, and this allows the excitation unit 12, the light receiving unit 13, the stimulant applying nozzle 14, and the spray nozzles 15A and 15B to be easily positioned. In addition, influence of absorption of light by the sample 91 can be reduced to perform more accurate measurement. It is in general preferable that the excitation unit 12 irradiates the sample 91 with the excitation light from one side, and that the light receiving unit 13 receives the light on the one side with respect to the sample 91.

It is also preferable that no gas exists on a propagation path of the excitation light from the excitation unit 12 to the sample 91 in the measurement space 10. Likewise, it is preferable that no gas exists on a propagation path of the light from the sample 91 to the light receiving unit 13. This causes no dew condensation on the optical path even if dew condensation occurs in the measurement space 10, and thus accurate measurement can be performed.

A light emitting element (e.g. a laser diode or a light emitting diode) serving as an excitation light source that generates excitation light in the excitation unit 12, as well as a light receiving element (e.g. a photodiode) serving as a photodetector that converts light into an electric signal in the light receiving unit 13 may be disposed in the measurement space 10 or outside the body case 20. In the latter case, excitation light output from the light emitting element outside the body case 20 enters from an input end of an optical fiber of the excitation unit 12, is guided into the measurement space 10 through the optical fiber, and then is emitted from an output end of the optical fiber to irradiate the sample 91. Light generated in the sample 91 is received at an input end of an optical fiber of the light receiving unit 13, is guided to the outside of the body case 20 through the optical fiber, and then is emitted from an output end of the optical fiber to be detected by the light receiving element. In a case where no fluorescence measurement and the like is performed, and then no excitation light is used, the excitation unit 12 is unnecessary.

The stimulant applying nozzle 14 is connected to a syringe disposed outside the body case 20 through a pipe to constitute a stimulant applying unit with these for applying a stimulant to the sample 91. Operating the syringe enables the stimulant to be applied to the sample 91 from a leading end of the stimulant applying nozzle 14. Application of the stimulant may vary an amount of light generated in the sample 91, and thus the sample 91 can be analyzed by measuring variation in the amount of generated light. Measuring the variation in the amount of generated light enables an effect of the stimulant to be evaluated. In a case where no stimulant is applied to the sample 91, the stimulant applying nozzle 14 is unnecessary.

The spray nozzles 15A and 15B constitute a spray unit along with an air pump 15C and a pipe 15D for spraying gas (e.g. air) on the sample 91 to agitate the sample 91. While one spray nozzle may be used, it is preferable to use a plurality of spray nozzles in the spray unit. The spray nozzles 15A and 15B spray the gas supplied from the air pump 15C through the pipe 15D on the sample 91 from a plurality of directions different from each other. The air pump 15C may be disposed in the measurement space 10, or outside the body case 20. Disposing the air pump 15C in the measurement space 10 enables the gas in the measurement space 10 to circulate.

Agitation by gas sprayed from the spray nozzles 15A and 15B enables, for example, mixing of the stimulant to be accelerated in the sample 91, and also enables aggregation of solid components to be prevented or eliminated in the sample 91. It is preferable that the spray nozzles 15A and 15B intermittently spray gas on the sample 91, and in this case, formation of a vortex in the sample 91 may be prevented.

It is also preferable that the spray nozzles 15A and 15B spray gas having controlled temperature or humidity on the sample 91, and it is further preferable that gas having controlled temperature and humidity is sprayed on the sample 91. In this case, temperature and humidity in the measurement space 10 can be maintained constant along with the heating unit 30 and the gas supplying unit 40.

The body case 20 includes an inner case 21 that surrounds the measurement space 10 in which the sample stage 11, the excitation unit 12, the light receiving unit 13, the stimulant applying nozzle 14, the spray nozzles 15A and 15B, and the like are disposed, and an outer case 22 that surrounds the inner case 21. The body case 20 shields the measurement space 10 from light from the outside, and seals the measurement space 10. The sealing by the body case 20 has to be of a level allowing temperature and humidity in the measurement space 10 to be controlled, at least. The body case 20 may include an inlet for guiding gas controlled at a constant temperature and a constant humidity into the measurement space 10 from the outside. The body case 20 also may include an outlet for exhausting gas from the measurement space 10 to the outside, as needed.

The body case 20 is detachable into a base portion and a top lid portion. To the base portion, the sample stage 11, the excitation unit 12, the light receiving unit 13, the stimulant applying nozzle 14, the spray nozzles 15A and 15B, and the like are attached. Removing the top lid portion allows operation such as placing the sample 91 on the sample stage 11, for example. Each of the base portion and the top lid portion of the body case 20 includes the corresponding inner case and outer case.

The heating unit 30 is disposed between the inner case 21 and the outer case 22 and adjusts temperature in the measurement space 10 through the inner case 21. Thus, it is preferable that thermal conductivity of the inner case 21 is higher than that of the outer case 22. The inner case 21 is preferably formed of a material with a high thermal conductivity (for example, metal such as copper and aluminum, ceramic such as alumina). The outer case 22 is preferably formed of a material with a low thermal conductivity (for example, resin, wood).

The heating unit 30, as described later for FIG. 2A and FIG. 2B, preferably includes a plurality of heating elements 31 being separately arranged in the periphery of the inner case 21 to control the temperature at a plurality of positions on the inner case 21. In a case where the inner case 21 is a rectangular parallelepiped, the heating unit 30 preferably controls the temperature at a plurality of positions on each of six faces of the inner case 21 by using the heating elements 31. This can facilitate temperature distribution of the whole of the inner case 21 to be uniform easily even if the inner case 21 has a low thermal conductivity, and thus can facilitate temperature distribution in the measurement space 10 to be uniform.

Each of the heating elements 31 is preferably an autonomous temperature control type element including a heater, a temperature sensor, and a controller that controls heating based on a measurement result by the temperature sensor. The heating element 31 employs autonomous temperature control type as described above to be easily arranged separately in the periphery of the inner case 21. This will be described later in detail.

The gas supplying unit 40 supplies gas (e.g. air) having controlled temperature and humidity into the measurement space 10 and adjusts temperature and humidity in the measurement space 10. The gas supplying unit 40 includes a humidifying unit 41, an adjusting unit 42, and an air pump 43 provided outside the body case 20 and generates gas having controlled temperature and humidity to supply the gas into the measurement space 10. This type of gas supplying unit 40 can efficiently generate gas having a predetermined temperature and a predetermined humidity to enable atmosphere in the measurement space 10 to be set at a predetermined temperature and a predetermined humidity in a short time.

The humidifying unit 41 includes a container 41A and a heating unit 41B provided in the periphery of the container 41A, and the heating unit 41B maintains water 41C contained in the container 41A at a predetermined temperature T1. The adjusting unit 42 includes a container 42A and a heating unit 42B provided in the periphery of the container 42A, and the heating unit 42B maintains water 42C contained in the container 42A at a predetermined temperature T2. The heating units 41B and 42B are preferably autonomous temperature control type units, respectively.

Gas taken into the air pump 43 through a pipe 44A is discharged into the water 41C in the container 41A of the humidifying unit 41 as bubbles from a nozzle at a leading end of a pipe 44B through the pipe 44B. Gas accumulated in an upper portion in the container 41A of the humidifying unit 41 is discharged into the water 42C in the container 42A of the adjusting unit 42 as bubbles from a nozzle at a leading end of a pipe 44C through the pipe 44C. Then, gas accumulated in an upper portion in the container 42A of the adjusting unit 42 is guided into the measurement space 10 through a pipe 44D.

The temperature T2 is lower than the temperature T1. Gas fed to the adjusting unit 42 from the humidifying unit 41 has the temperature T1 and a high humidity. The humidity of the gas is set to a level that causes dew condensation when the temperature of the gas decreases from T1 to T2. The humidity of the gas fed to the adjusting unit 42 increases, as the temperature of the gas decreases to T2, thereby being able to reach 100%. The adjusting unit 42 also serves as a dew condensation trap. Gas guided into the measurement space 10 from the adjusting unit 42 has the temperature T2 and a humidity of 100%.

The pipe 44C for feeding gas to the adjusting unit 42 from the humidifying unit 41 is preferably provided with a thermal insulation cover 45C in the periphery of the pipe 44C. In addition, the pipe 44D for feeding gas to the measurement space 10 from the adjusting unit 42 is preferably provided with a thermal insulation cover 45D in the periphery of the pipe 44D. This can prevent temperature from decreasing during a period in which warmed gas is fed through the pipe.

The other end of the pipe 44A connected to a gas inlet of the air pump 43 may be placed outside the body case 20 or in the measurement space 10. The latter case enables warmed and humidified gas to circulate to improve energy efficiency as well as problems of exhaust treatment to be reduced.

In the case where the sample 91 is blood, for example, temperature in the measurement space 10 is preferably 37° C. to maintain activity of cells, and in addition, humidity in the measurement space 10 is preferably 100% to reduce evaporation. Thus, the temperature T2 of the water 42C contained in the container 42A of the adjusting unit 42 is set at 37° C., and the temperature T1 of the water 41C contained in the container 41A of the humidifying unit 41 is set at 40° C., for example. Gas sprayed from the spray nozzles 15A and 15B also preferably has a temperature of 37° C. and a humidity of 100%.

In addition to gas having a temperature of 37° C. and a humidity of 100% supplied into the measurement space 10 by using the gas supplying unit 40, the heating unit 30 disposed between the inner case 21 and the outer case 22 enables temperature in the measurement space 10 to be maintained at 37° C. through the inner case 21. In this case, all objects existing in the measurement space 10, including the inner case 21, have a substantially uniform temperature of 37° C. to cause the gas in the measurement space 10 to have a humidity of 100%.

Thus, the present embodiment enables evaporation of liquid in the sample 91 to be reduced to reduce variation in concentration of the sample. The present embodiment also can reduce evaporation of liquid caused by gas spray when the sample 91 is agitated by the gas spray from the spray nozzles 15A and 15B for uniformity of the sample 91 to accelerate mixing of the stimulant in the sample 91, or to prevent or eliminate aggregation of solid components in the sample 91, and thus variation in concentration of the sample can be reduced. The measurement apparatus 1 configured as described above enables the measurement space 10, in which the sample 91 is to be placed, to be maintained at a constant temperature and a constant humidity to reduce evaporation of the sample 91 to enable accurate measurement.

Next, a configuration example of the heating unit 30 will be described with reference to FIG. 2A, FIG. 2B, and FIG. 3. The heating units 41B and 42B can be configured similarly.

Figure 2A:
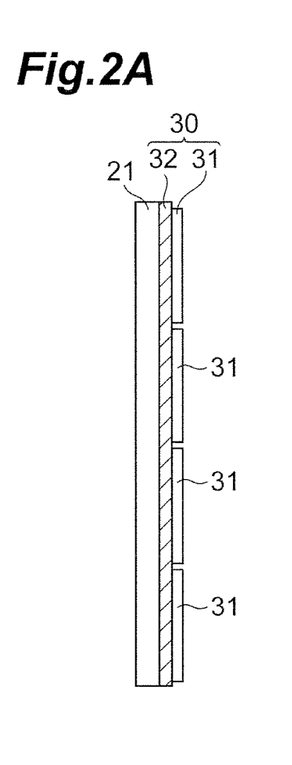
FIG. 2A and FIG. 2B are a sectional view and a plan view, respectively, to illustrate a configuration example of a heating unit 30.
Figure 2B:
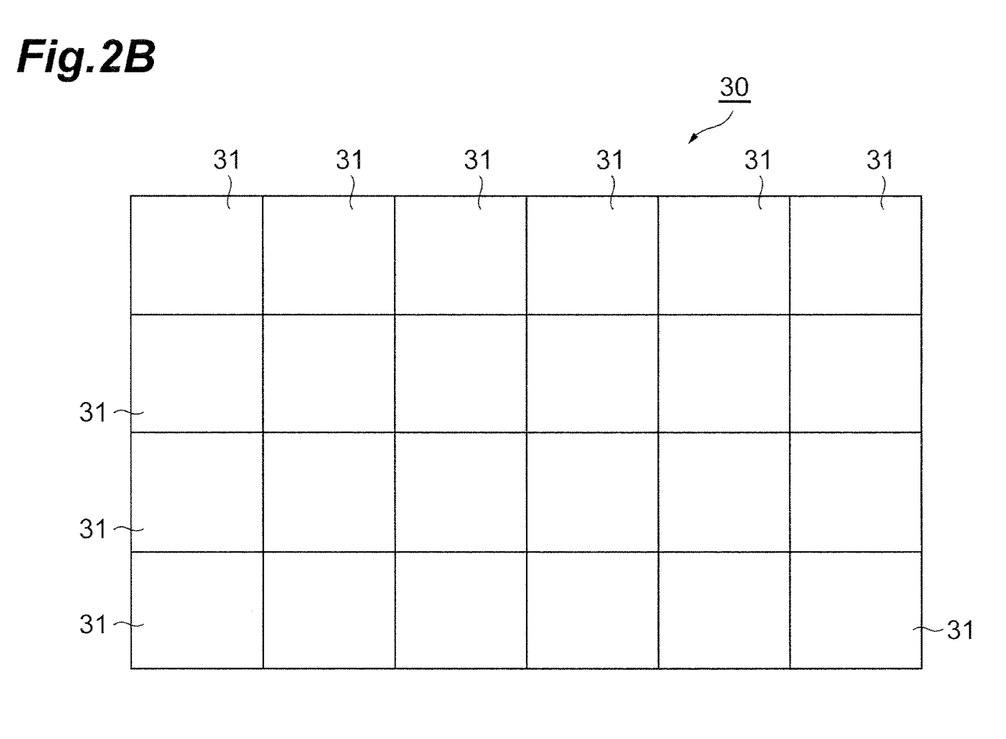

FIG. 2A is a sectional view of the inner case 21 and the heating unit 30. FIG. 2B is a plan view illustrating arrangement of the plurality of heating elements 31 in the heating unit 30. These figures illustrate a configuration example of the heating unit 30 on one face of a plurality of faces constituting the inner case 21. The heating unit 30, as illustrate in FIG. 1, is disposed between the inner case 21 and the outer case 22 to adjust temperature in the measurement space 10 through the inner case 21. The heating unit 30 includes a plurality of heating elements 31 (4×6 elements in FIG. 2A and FIG. 2B) that are two-dimensionally arrayed on a substrate 32. The substrate 32 includes a plurality of through vias between one principal surface provided with the heating elements 31, and the other principal surface to be brought into contact with the inner case 21. Heat of the heaters of the heating elements 31 is conducted to the measurement space 10 through the through vias of the substrate 32 and the inner case 21. The substrate 32 is preferably formed of a material with a large thermal conductivity (for example, ceramic such as alumina).

Figure 3:
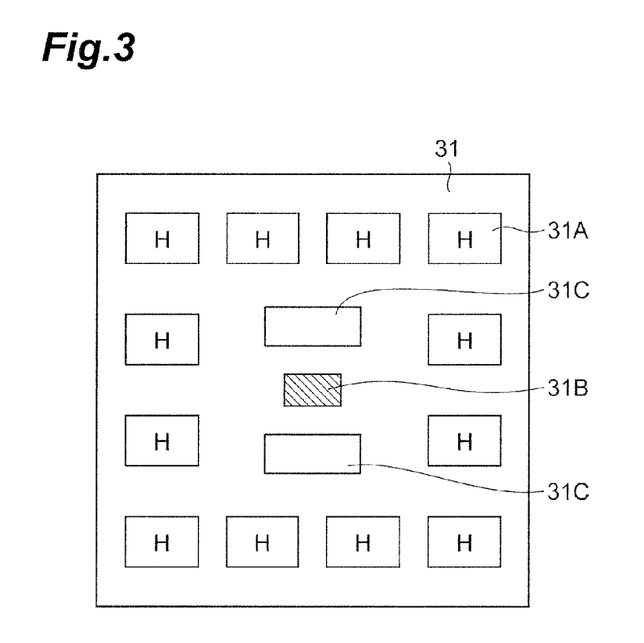
FIG. 3 illustrates a configuration example of a heating element 31.

FIG. 3 illustrates a configuration example of the heating element 31. Each of the heating elements 31, for example, includes a plurality of heaters 31A (12 heaters in FIG. 3), a temperature sensor 31B, and a controller 31C, in a rectangular region of about 20 mm×20 mm and is configured as an autonomous temperature control type element. The controller 31C controls heating by each of the heaters 31A based on a measurement result of temperature by the temperature sensor 31B. The temperature sensor 31B is arranged in a central portion of the heating element 31, and the heaters 31A are arranged around the temperature sensor 31B, thereby enabling uniform heating. Each of the heaters 31A, for example, includes a surface-mounted chip resistor.

Subsequently, a measurement example using the measurement apparatus 1 of the present embodiment will be described. In the measurement example described below, myeloperoxidase activity and superoxide ($O_2^-$) production activity are simultaneously measured by using the same sample containing whole blood to evaluate activity of neutrophilic cells based on measurement data on the sample.

The neutrophil is a kind of leukocyte. The neutrophil primarily serves to sterilize bacteria and Eumycetes invaded into a living body by phagocytosis to prevent infection. The neutrophil takes bacteria and the like into a neutrophil such that the bacteria are enclosed by a neutrophil's plasma membrane, and then forms a phagosome. Subsequently, the phagosome fuses with a granulation, and a granular content is discharged into the phagosome. Then, an NADPH oxidase system formed in a cell membrane (membrane of the phagosome) generates reactive oxygen (superoxide, hydrogen peroxide), and the reactive oxygen sterilizes the bacteria and the like. In addition, an enzyme reaction of myeloperoxidase (EC No. 1.11.2.2) contained in the granular content produces hypochlorous acid (HOCl) (or its halogen equivalent) from the hydrogen peroxide ($H_2O_2$) and a chlorine ion ($Cl^-$), and the hypochlorous acid sterilizes the bacteria and the like. Thus, activity of the neutrophil can be evaluated by using myeloperoxidase activity and superoxide production activity as an index.

The sample 91 contains whole blood. The "whole blood" means blood itself collected from a living body. The sample 91 may be the whole blood itself, or may be formed by diluting the whole blood with physiological saline solution, buffer solution, or the like. In the case of dilution, a dilution rate may be appropriately set, and may be diluted about 100 times, for example. A minute amount of peripheral blood (2 to 3 µL) may be collected from a fingertip or the like by using a blood collecting tool (e.g. a lancet) to be used by a diabetic to daily measure its blood sugar level, and the collected blood may be used as the sample 91. This kind of minute amount of blood has a load that is so small that activity of a neutrophil can be evaluated daily.

The sample 91, into which a fluorescent indicator and a chemiluminescent indicator are added, is placed on the preparation 90, and the preparation 90 is placed on the sample stage 11. Aminophenyl Fluorescein (APF), for example, is used as the fluorescent indicator. When the APF as the fluorescent indicator reacts with HOCl, irradiation with excitation light of a wavelength of about 490 nm generates fluorescence of a wavelength of about 515 nm, and as a result, myeloperoxidase activity can be measured by detecting fluorescence having the wavelength. As the chemiluminescent indicator, 2-Methyl-6-(4-methoxyphenyl)-3,7-dihydroimidazo[1,2-a]pyrazin-3-one (MCLA) is used, for example. When the MCLA as the chemiluminescent indicator reacts with superoxide, chemiluminescence having a maximum emission wavelength of about 465 nm is generated, and as a result, superoxide production activity can be measured by detecting chemiluminescence having the wavelength.

When the sample 91 is placed on the sample stage 11, the top lid portion is placed on the base portion of the body case 20, and the measurement space 10 is then shielded from light and sealed. After that, the heating unit 30 and the gas supplying unit 40 maintain the measurement space 10 to have a temperature of 37° C. and a humidity of 100%, and then measurement starts. Before the sample 91 is placed on the sample stage 11, it is preferable to previously set the measurement space 10 to have a temperature of 37° C. and a humidity of 100%.

The sample 91 placed on the sample stage 11 is intermittently irradiated with excitation light from the excitation unit 12. An irradiation period of the excitation light and a non-irradiation period thereof are repeated with a constant period. During the irradiation period of the excitation light, the light receiving unit 13 receives fluorescence and chemiluminescence generated in the sample 91 to acquire an electric signal value V1 corresponding to an amount of light received. During the non-irradiation period, the light receiving unit 13 receives chemiluminescence generated in the sample 91 to acquire an electric signal value V2 corresponding to an amount of light received. Fluorescence intensity (i.e. a measurement value of myeloperoxidase activity) can be acquired from a value acquired by subtracting the electric signal value V2 from the electric signal value V1. Chemiluminescence intensity (i.e. a measurement value of superoxide production activity) can be acquired from the electric signal value V2. In this way, the present measurement example enables both the activities to be simultaneously measured under the same condition, and thus activity of a neutrophil can be more accurately evaluated.

The stimulant applying nozzle 14 applies a stimulant to the sample 91 midway through the measurement period, as needed. The stimulant may be any substance that activates a function of a neutrophil (e.g. migration, phagocytosis). As a neutrophilic stimulant, N-formyl-L-methionyl-L-leucyl-phenylalanine (fMLP) is used, for example. Adding the neutrophilic stimulant to the sample 91 applies pseudo-stimulus to a neutrophil in the sample 91 to cause an innate immune response (biological defense response), enabling infection defense ability of the neutrophil to be evaluated. In the case where the pseudo-stimulus is not applied, a neutrophil existing in peripheral blood, as it is, can be evaluated, and thus, for example, it is possible to early evaluate a state where a neutrophil is excessively activated to produce reactive oxygen due to vigorous exercise, smoking, or the like (oxidative stress state). In addition, it is also possible to evaluate ability of suppressing excessive neutrophilic activation caused by food and drink in a living body (called also antioxidant ability or anti oxidative stress ability).

Throughout a period in which this kind of measurement is performed, the measurement space 10 is maintained to have a temperature of 37° C. and a humidity of 100% by the heating unit 30 and the gas supplying unit 40, and thus evaporation of the sample 91 is reduced. In addition, the sample 91 is agitated by gas spray from the spray nozzles 15A and 15B, and thus mixing of a stimulant is accelerated, as well as aggregation of solid components (blood cells) in the sample 91 is prevented or eliminated. As a result, myeloperoxidase activity and superoxide production activity can be accurately measured, and thus activity of a neutrophil can be accurately evaluated based on the measurement values.

Second Embodiment

Figure 4:
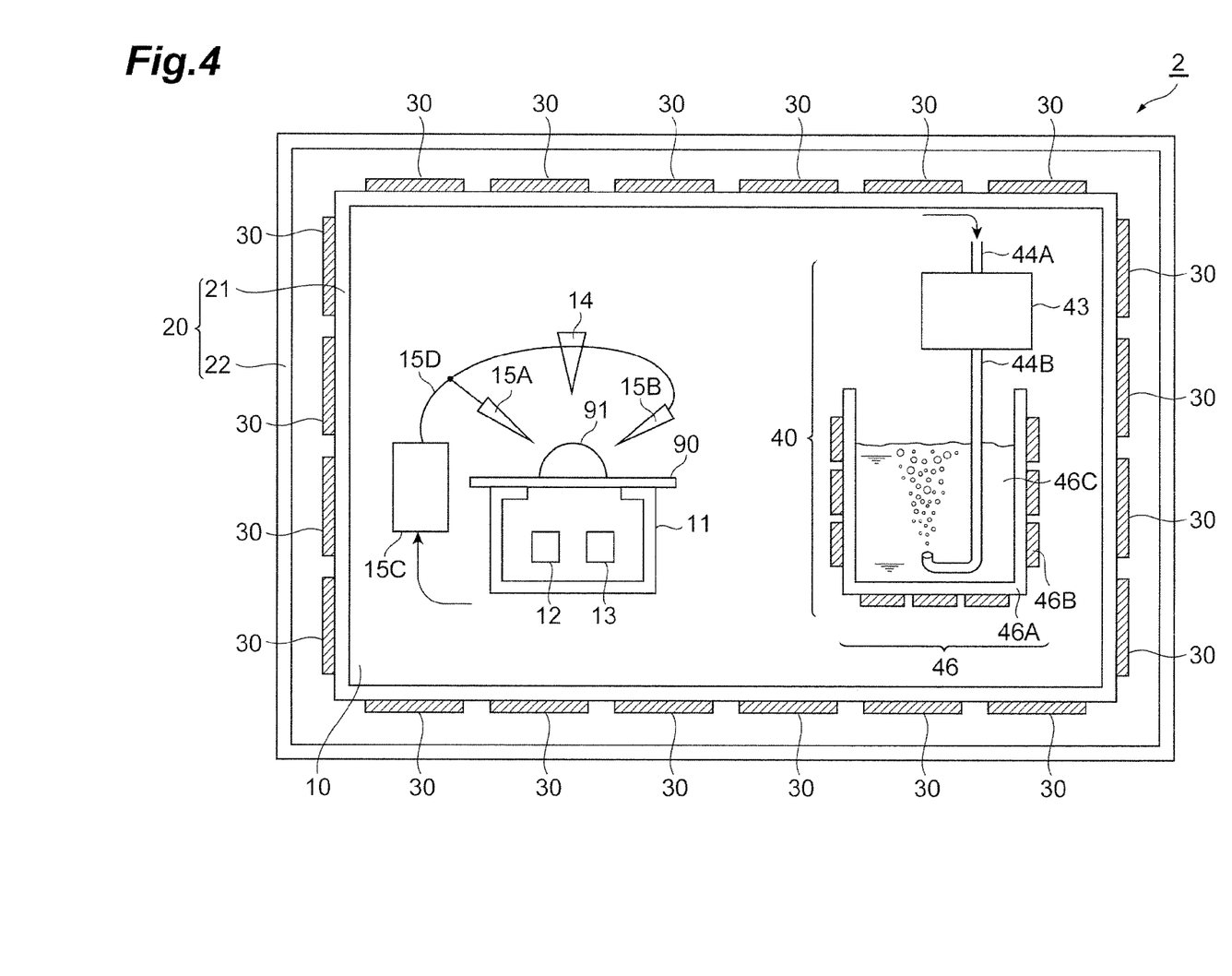
FIG. 4 illustrates a configuration of a measurement apparatus 2 of a second embodiment.

FIG. 4 illustrates a configuration of a measurement apparatus 2 according to a second embodiment. The measurement apparatus 2 includes a sample stage 11, an excitation unit 12, a light receiving unit 13, a stimulant applying nozzle 14, spray nozzles 15A and 15B, and the like in a measurement space 10 inside a body case 20. The measurement apparatus 2 further includes a heating unit 30 and a gas supplying unit 40. As compared with the configuration of the measurement apparatus 1 of the first embodiment illustrated in FIG. 1, the measurement apparatus 2 of the second embodiment illustrated in FIG. 4 is different in that the gas supplying unit 40 is provided in the measurement space 10.

The gas supplying unit 40 supplies gas (e.g. air) having controlled temperature and humidity into the measurement space 10 to adjust temperature and humidity in the measurement space 10. The gas supplying unit 40 includes a humidifying unit 46 and an air pump 43, provided in the measurement space 10, to generate gas having controlled temperature and humidity and supply the gas into the measurement space 10. The humidifying unit 46 includes a container 46A and a heating unit 46B provided in the periphery of the container 46A, and the heating unit 46B maintains water 46C contained in the container 46A at a predetermined temperature. The heating unit 46B is preferably an autonomous temperature control type unit.

Gas in the measurement space 10 is taken into the air pump 43 through a pipe 44A, and is discharged into the water 46C in the container 46A of the humidifying unit 46 as bubbles from a nozzle at a leading end of a pipe 44B through the pipe 44B. The bubbles are discharged into the measurement space 10 as warmed and humidified gas.

The measurement apparatus 2 of the second embodiment also operates as with the first embodiment to achieve the same effect. In the second embodiment, warmed and humidified gas can be circulated, and thus energy efficiency can be improved and problems of exhaust treatment can be reduced.

The measurement apparatus according to the present invention is not limited to the embodiments and the configuration examples described above, and can be variously modified.

The measurement apparatus according to the above embodiment includes (1) a sample stage on which a sample is placed, (2) a light receiving unit that receives light generated in the sample, (3) a spray nozzle that sprays gas on the sample to agitate the sample, (4) a body case that includes an inner case surrounding a measurement space in which the sample stage, the light receiving unit, and the spray nozzle are disposed, and an outer case surrounding the inner case, the body case shielding the measurement space from light from the outside, (5) a heating unit that is disposed between the inner case and the outer case and adjusts temperature in the measurement space through the inner case, and (6) a gas supplying unit that supplies gas having controlled temperature and humidity into the measurement space and adjusts temperature and humidity in the measurement space.

In the measurement apparatus described above, the heating unit may be configured to include a plurality of heating elements being separately arranged in the periphery of the inner case. In this case, each of the plurality of heating elements may be configured as an autonomous temperature control type element including a heater, a temperature sensor, and a controller that controls heating by the heater based on a measurement result by the temperature sensor.

The measurement apparatus described above may be configured so that the gas supplying unit takes in air from the outside of the body case and supplies gas having controlled temperature and humidity into the measurement space. In addition, the measurement apparatus described above may be configured so that the gas supplying unit takes in air in the measurement space and supplies gas having controlled temperature and humidity into the measurement space.

The measurement apparatus described above may further include an excitation unit being disposed in the measurement space and irradiating the sample with excitation light. In this case, the excitation unit may be configured to irradiate the sample with excitation light from one side, and the light receiving unit may be configured to receive light on the one side with respect to the sample.

The measurement apparatus described above may be configured to further include a stimulant applying nozzle being disposed in the measurement space and applying a stimulant to the sample.

In the measurement apparatus described above, the spray nozzle may be configured to spray gas on the sample from a plurality of directions. In addition, the spray nozzle may be configured to intermittently spray gas on the sample. Further, the spray nozzle may be configured to spray gas having controlled temperature or humidity on the sample.

The present invention is available as a measurement apparatus capable of accurate measurement.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A measurement apparatus comprising:
   a sample stage on which a sample is placed;
   a light receiving unit receiving light generated in the sample;
   a spray nozzle spraying gas on the sample to agitate the sample;
   a body case including an inner case that surrounds a measurement space in which the sample stage, the light receiving unit, and the spray nozzle are disposed, and an outer case that surrounds the inner case, the body case shielding the measurement space from light from the outside;
   a heating unit being disposed between the inner case and the outer case and adjusting temperature in the measurement space through the inner case; and
   a gas supplying unit supplying gas having controlled temperature and humidity into the measurement space and adjusting temperature and humidity in the measurement space.

2. The measurement apparatus according to claim 1, wherein the heating unit includes a plurality of heating elements being separately arranged in the periphery of the inner case.

3. The measurement apparatus according to claim 2, wherein each of the plurality of heating elements is an autonomous temperature control type element including a heater, a temperature sensor, and a controller that controls heating by the heater based on a measurement result by the temperature sensor.

4. The measurement apparatus according to claim 1, wherein the gas supplying unit takes in air from the outside of the body case and supplies gas having controlled temperature and humidity into the measurement space.

5. The measurement apparatus according to claim 1, wherein the gas supplying unit takes in air in the measurement space and supplies gas having controlled temperature and humidity into the measurement space.

6. The measurement apparatus according to claim 1, further comprising an excitation unit being disposed in the measurement space and irradiating the sample with excitation light.

7. The measurement apparatus according to claim 6, wherein the excitation unit irradiates the sample with excitation light from one side, and the light receiving unit receives light on the one side with respect to the sample.

8. The measurement apparatus according to claim 1, further comprising a stimulant applying nozzle being disposed in the measurement space and applying a stimulant to the sample.

9. The measurement apparatus according to claim 1, wherein the spray nozzle sprays gas on the sample from a plurality of directions.

10. The measurement apparatus according to claim 1, wherein the spray nozzle intermittently sprays gas on the sample.

11. The measurement apparatus according to claim 1, wherein the spray nozzle sprays gas having controlled temperature or humidity on the sample.

* * * * *